United States Patent
Pipenhagen et al.

(10) Patent No.: US 8,038,687 B2
(45) Date of Patent: Oct. 18, 2011

(54) SUTURE LOOP CLOSURE DEVICE

(75) Inventors: Catherine A. Pipenhagen, Chanhassen, MN (US); John Avi Roop, Crystal, MN (US); Kedar R. Belhe, Minnetonka, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1686 days.

(21) Appl. No.: 11/130,916

(22) Filed: May 17, 2005

(65) Prior Publication Data
US 2006/0264975 A1    Nov. 23, 2006

(51) Int. Cl.
*A61B 17/04* (2006.01)

(52) U.S. Cl. ......... 606/144; 606/145; 606/139; 606/148

(58) Field of Classification Search .................. 606/139, 606/144–151, 142, 213
See application file for complete search history.

(56) References Cited

U.S. PATENT DOCUMENTS

| | | | |
|---|---|---|---|
| 4,602,635 A | 7/1986 | Mulhollan et al. | |
| 5,304,184 A | 4/1994 | Hathaway et al. | |
| 5,376,096 A | 12/1994 | Foster | |
| 5,403,329 A | 4/1995 | Hinchcliffe | |
| 5,411,520 A | 5/1995 | Nash et al. | |
| 5,417,699 A | 5/1995 | Klein | |
| 5,431,666 A | 7/1995 | Sauer et al. | |
| 5,454,820 A * | 10/1995 | Kammerer et al. | 606/148 |
| 5,462,561 A | 10/1995 | Voda | |
| 5,476,469 A | 12/1995 | Hathaway et al. | |
| 5,496,332 A | 3/1996 | Sierra et al. | |
| 5,507,757 A | 4/1996 | Sauer et al. | |
| 5,527,322 A | 6/1996 | Klein | |
| 5,549,633 A | 8/1996 | Evans et al. | |
| 5,613,974 A | 3/1997 | Andreas et al. | |
| 5,626,588 A | 5/1997 | Sauer et al. | |
| 5,662,681 A | 9/1997 | Nash et al. | |
| 5,700,273 A * | 12/1997 | Buelna et al. | 606/148 |
| 5,720,757 A | 2/1998 | Hathaway et al. | |
| 5,746,755 A | 5/1998 | Wood et al. | |
| 5,755,727 A | 5/1998 | Kontos | |
| 5,766,183 A | 6/1998 | Sauer | |
| 5,779,719 A | 7/1998 | Klein et al. | |
| 5,782,861 A | 7/1998 | Cragg et al. | |
| 5,797,928 A * | 8/1998 | Kogasaka | 606/144 |
| 5,797,929 A | 8/1998 | Andreas et al. | |
| 5,855,585 A | 1/1999 | Kontos | |
| 5,860,990 A | 1/1999 | Nobles et al. | |
| 5,868,762 A | 2/1999 | Cragg et al. | |
| 5,876,411 A | 3/1999 | Kontos | |
| 5,902,311 A | 5/1999 | Andreas et al. | |
| 5,919,207 A | 7/1999 | Taheri | |
| 5,980,539 A | 11/1999 | Kontos | |
| 5,984,950 A | 11/1999 | Cragg et al. | |
| 6,042,601 A | 3/2000 | Smith | |
| 6,117,144 A * | 9/2000 | Nobles et al. | 606/144 |
| 6,132,439 A | 10/2000 | Kontos | |
| 6,171,317 B1 | 1/2001 | Jackson et al. | |
| 6,231,561 B1 | 5/2001 | Frazier et al. | |
| 6,425,887 B1 * | 7/2002 | McGuckin et al. | 604/272 |
| 2003/0093093 A1 * | 5/2003 | Modesitt et al. | 606/144 |

* cited by examiner

*Primary Examiner* — Corrine M McDermott
*Assistant Examiner* — Mark Mashack
(74) *Attorney, Agent, or Firm* — Holland & Hart (57) ABSTRACT

The present invention describes apparatus and methods for tying a filament across subcutaneous punctures. According to some embodiments, the apparatus and methods provide pre-tied knots that are inserted into a bodily lumen. Needles flanking the subcutaneous puncture are inserted into the lumen and grab the pre-tied knots. The pre-tied knots are pulled through tiny holes flanking the subcutaneous puncture by the needles, leaving an internal length of the filament across the subcutaneous puncture. The filament is then externally tied, closing the subcutaneous puncture.

11 Claims, 8 Drawing Sheets

SUTURE LOOP CLOSURE DEVICE

FIELD OF THE INVENTION

This invention relates generally to medical devices and more particularly to suturing devices for closing a hole in a corporeal vessel wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery. The insertion sheath enables the introduction of other instruments (e.g., a catheter) to an operative position within the vascular system. Intravascular and intraluminal procedures unavoidably present the problem of stopping the bleeding at the percutaneous puncture after the procedure has been completed and after the instrument (and any insertion sheaths used therewith) has been removed. Bleeding from puncture sites, particularly in the case of femoral arterial punctures, is typically stopped by utilizing vascular closure devices, such as those described in U.S. Pat. Nos. 6,179,863; 6,090,130; and 6,045,569, which are hereby incorporated by this reference.

The above patents describe a tissue puncture closure device in which, generically, a suture filament is pre-threaded through an elongated sheath (used to access the tissue puncture), through an anchor exterior to the distal tip of the sheath, and then back into the sheath where it is attached to a sealing plug disposed on the suture filament line within the sheath. The sheath is inserted through an incision in the skin and through the puncture in the tissue wall until the anchor is deployed within the luminal cavity of the organ or artery, with the sealing plug remaining outside the luminal cavity. Successful deployment of the sealing plug requires that the sealing plug be manually ejected from within the sheath and tamped down to the outer surface of the tissue puncture using a tamping tube, while simultaneously pulling on the filament to cinch tight the filament connecting the anchor and sealing plug. The anchor and the sealing plug are brought together in a pulley-like fashion with a self-tightening slip-knot in the filament, such that the tissue puncture is sandwiched between the anchor and sealing plug, thereby sealing the tissue puncture and stopping bleeding.

Using the prior devices, however, there is a risk of inserting the sealing plug into the artery. Complications may arise if the sealing plug enters the artery. In addition, the sealing plug may not be deployed close enough to the hole to effectively seal the puncture, which may result in prolonged bleeding and slower recovery. Some doctors would prefer to close the puncture instead by tying a suture across the hole. However, normally the puncture is relatively small, and often inaccessible through the incision leading to the puncture.

SUMMARY

In one of many possible embodiments, the present invention provides a tissue puncture closure device. The tissue puncture closure device comprises a central shaft having first and second end portions and a slotted portion disposed between the first and second end portions, a filament extending from the first portion to the second portion, and first and second open loop knots disposed at least partially within the slotted portion. The slotted portion may comprise first and second elongated slots receptive of a needle. The slotted portion may also comprise third and fourth slots, wherein the third and fourth slots comprise a smaller width than the first and second slots. First portions of the first and second open loop knots may extend at least partially through the third slot, and second portions of the first and second open loop knots extend at least partially through the fourth slot. The first, second, third, and fourth slots may be arranged approximately 90 degrees from one another such that the first and second slots are substantially opposite of one another, and the third and fourth slots are substantially opposite of one another.

According to some aspects, the central shaft extends through a vascular access sheath. In addition, a first curved needle may extend through a first side port in the vascular access sheath, into the slotted portion, and at least partially through the first open loop knot. Similarly, a second curved needle may extend through a second side port in the vascular access sheath, into the slotted portion, and at least partially through the second open loop knot.

According to some embodiments, a first cannula needle extends through a first side port in the vascular access sheath and diverges from the vascular access sheath. A first needle passes through the first cannula needle, curves into the slotted portion, and extends at least partially through the first open loop knot. A second cannula needle extends through a second side port in the vascular access sheath and diverges from the vascular access sheath. A second needle extends through the second cannula needle, curves into the slotted portion, and extends at least partially through the second open loop knot. According to some aspects, the first and second open loop knots are remotely tightenable.

Other aspects of the invention provide a vascular closure system. The vascular closure system comprises a closure device including a central shaft having an open channel portion disposed between first and second end portions, and a filament looping through the central shaft such that the filament is tied into first and second open knots at the open channel portion. The system may include a vascular access sheath receptive of the closure device. The central shaft may include first and second end portions flanking the open channel portion such that the filament extends from the first end portion, to the second end portion, and back to the first end portion. One or more free ends of the filament are accessible to an operator. The system may also include first and second cannula needles extending through first and second side ports, respectively, in the vascular access sheath, a first curved needle extending through the first cannula needle, into the open channel portion, and partially through the first open loop knot, a second curved needle extending through the second cannula needle, into the open channel portion, and partially through the second open loop knot, such that each of the first and second curved needles comprises a step at an end thereof. Each of the first and second curved needles may comprises a nitinol needle having sufficient elasticity to pass through the first and second straight cannula needles and return to a curved shape after passing through ends thereof. The first and second open knots may be remotely tightenable against the steps of the first and second curved needles, respectively, by applying tension to the filament.

Another aspect of the invention provides a vascular closure system comprising a vascular access sheath having a plurality of side-ports disposed at a distal end portion, an open-loop knot carrying device insertable into the vascular access sheath, a plurality of cannula needles, each of the plurality of cannula needles insertable through a corresponding one of the plurality of side-ports, and a plurality of curved needles. Each of the plurality of curved needles is insertable through a corresponding one of the plurality of cannula needles.

Another aspect of the invention provides a method of closing a subcutaneous puncture. The method comprises inserting a filament into a lumen through the puncture, inserting first and second needles into the lumen through holes flanking the puncture, grabbing the filament with each of the first and second needles, retracting the filament through the holes flanking the puncture, and tying the filament across the puncture. The method may also include inserting first and second cannula needles into the lumen to create the flanking holes.

According to some aspects of the invention, the grabbing comprises passing the first needle partially through a first open-loop knot disposed in the filament inside the lumen, passing the second needle partially through a second open-loop knot disposed in the filament inside the lumen, and remotely cinching the first and second open-loop knots around the first and second needles, respectively. The inserting of the filament may comprise passing a shaft through a vascular access sheath, such that the filament traverses the shaft and is pre-tied into first and second open-loop knots at a slotted portion of the shaft.

Another aspect of the invention provides a method of closing a subcutaneous puncture. The method includes inserting a tubular shaft comprising a filament having first and second open-loop knots into a lumen through the puncture, advancing first and second cannula needles flanking and spaced from the tubular shaft into the lumen, passing first and second curved needles through the first and second cannula needles, respectively, cinching the first and second open-loop knots to the first and second curved needles, respectively, retracting the first and second curved needles through the first and second cannula needles, respectively, and tying the filament across the puncture.

Another aspect of the invention provides a method of making a subcutaneous puncture closure device, comprising providing a tubular shaft having a slotted portion, tying first and second knots in a filament, inserting the filament into a tubular shaft, placing first portions of the first and second knots in a first slot of the slotted portion, and placing second portions of the first and second knots in a second slot of the slotted portion.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is not properly seated against an exterior situs of the arteriotomy. If the plug does not seat against the arteriotomy, there is a potential for elongated bleeding. The present invention describes methods and apparatus to tie a suture across an arteriotomy. While the vascular instruments shown and described below include certain insertion sheaths and puncture sealing devices, the application of principles described herein to are not limited to the specific devices shown. The principles described herein may be used with any vascular closure device. Therefore, while the description below is directed primarily to arterial procedures and certain embodiments of a vascular closure device, the methods and apparatus are only limited by the appended claims.

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen sponge 1 10. The collagen sponge 1 10 is slidingly attached to the suture 104 as the suture passes distally through the carrier tube 102, but as the suture traverses the anchor 108 and reenters the carrier tube 102, it is securely slip knotted proximal to the collagen sponge 110 to facilitate cinching of the collagen sponge 110 when the closure device 100 is properly placed and the anchor 108 deployed (see FIG. 4).

Figure 1:
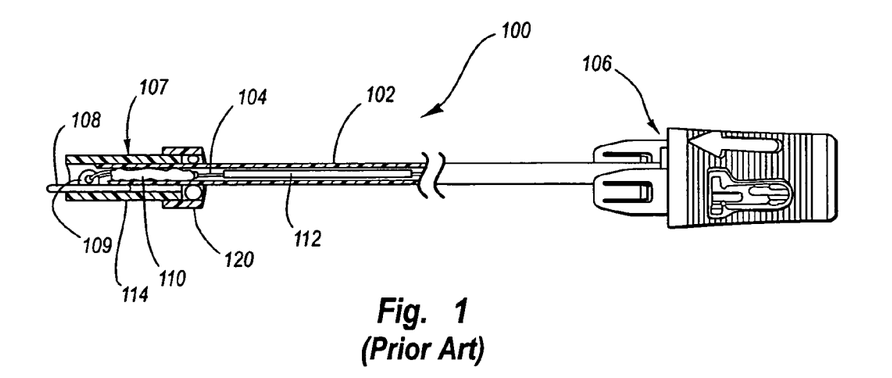
FIG. 1 is a side view, partly in section, of an internal tissue puncture closure device according to the prior art.

The carrier tube 102 typically includes a tamping tube 112 disposed therein. The tamping tube 112 is slidingly mounted on the suture 104 and may be used by an operator to tamp the collagen sponge 110 toward the anchor 108 at an appropriate time to plug a percutaneous tissue puncture. Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
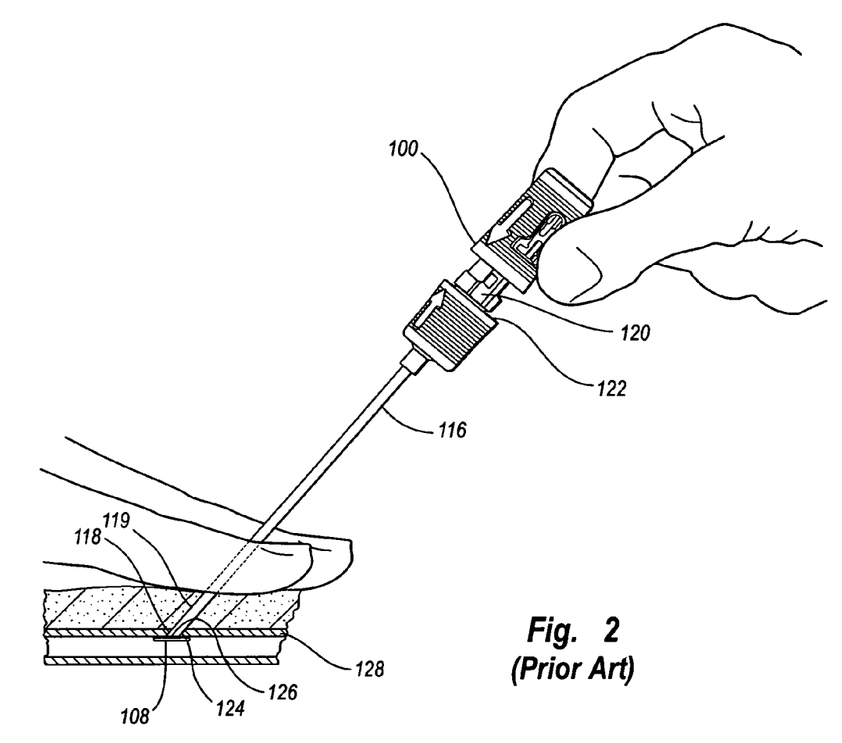
FIG. 2 is a side view of the tissue puncture closure device of FIG. 1 inserted through an insertion sheath and engaged with an artery, the artery shown in section, according to the prior art.
Figure 3:
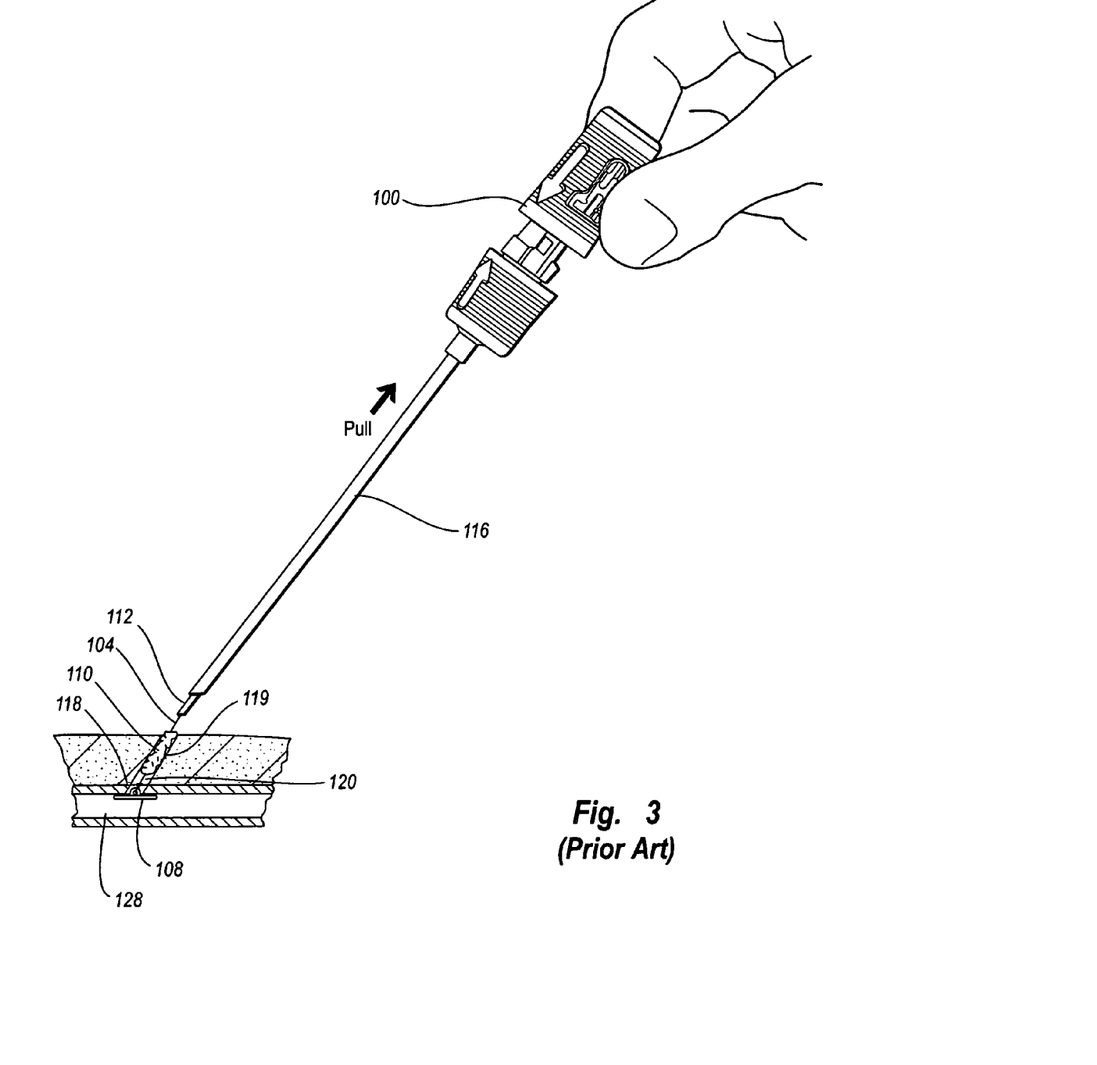
FIG. 3 is a side view of the tissue puncture closure device, insertion sheath, and artery of FIG. 2, wherein the tissue closure device and insertion sheath are being withdrawn from the artery to deploy a collagen sponge according to the prior art.
Figure 4:
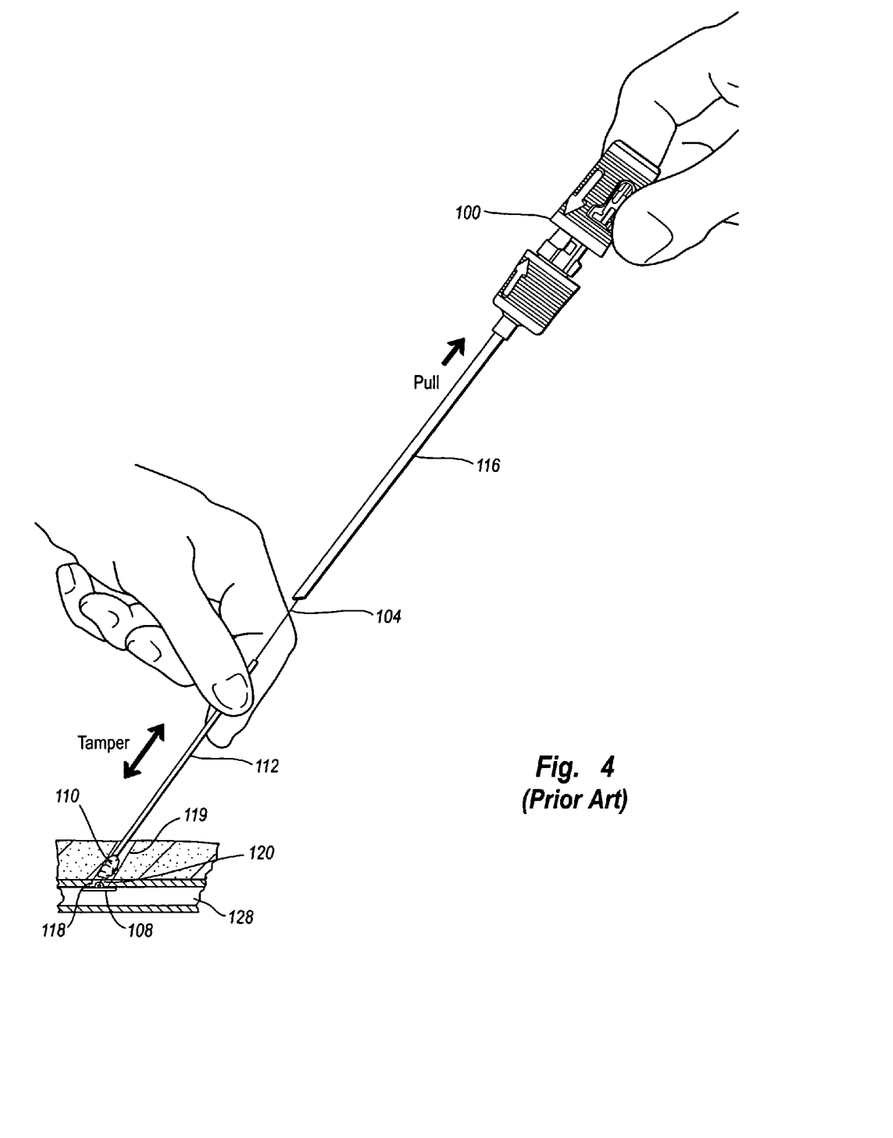
FIG. 4 is a side view of the tissue puncture closure device, insertion sheath, and artery shown in FIG. 3 with a tamping tube fully exposed and being used to tamp the collagen sponge according to the prior art.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 (FIG. 1) from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114 (FIG. 1), releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, depositing the collagen sponge 110 in the incision tract 119 and exposing the tamping tube 112. With the tamping tube 112 fully exposed as shown in FIG. 4, the collagen sponge 110 is manually tamped, and the anchor 108 and collagen sponge 110 are cinched together and held in place with a self-tightening slipknot on the suture 102. Thus, the tissue puncture 118 is sandwiched between and sealed by the anchor 108 and the collagen sponge 110. The suture 104 is then cut and the incision 119 may be closed. The suture 104, anchor 108, and collagen sponge 110 are generally made of resorbable materials and therefore remain in place while the puncture 118 heals.

Using the typical tissue puncture closure device 100 described above, however, the tamping of the collagen sponge 110 cannot commence until the sheath 116 has been removed and the tamping tube 112 is exposed for manual grasping. Under certain conditions, removal of the sheath 116 prior to tamping the collagen sponge 110 causes the collagen sponge 110 to retract from the tissue puncture 118, creating a gap 120 between the collagen sponge 110 and the puncture 118. The gap 120 may remain even after tamping as shown in FIG. 4, and sometimes results in only a partial seal and bleeding from the tissue puncture 118. In addition, excess tamping may cause the collagen sponge 110 to enter the artery.

Therefore, the present specification describes a tissue puncture closure device that enables tying sutures across punctures, rather than sandwiching punctures between internal and external components. As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figures 5A, 5B:
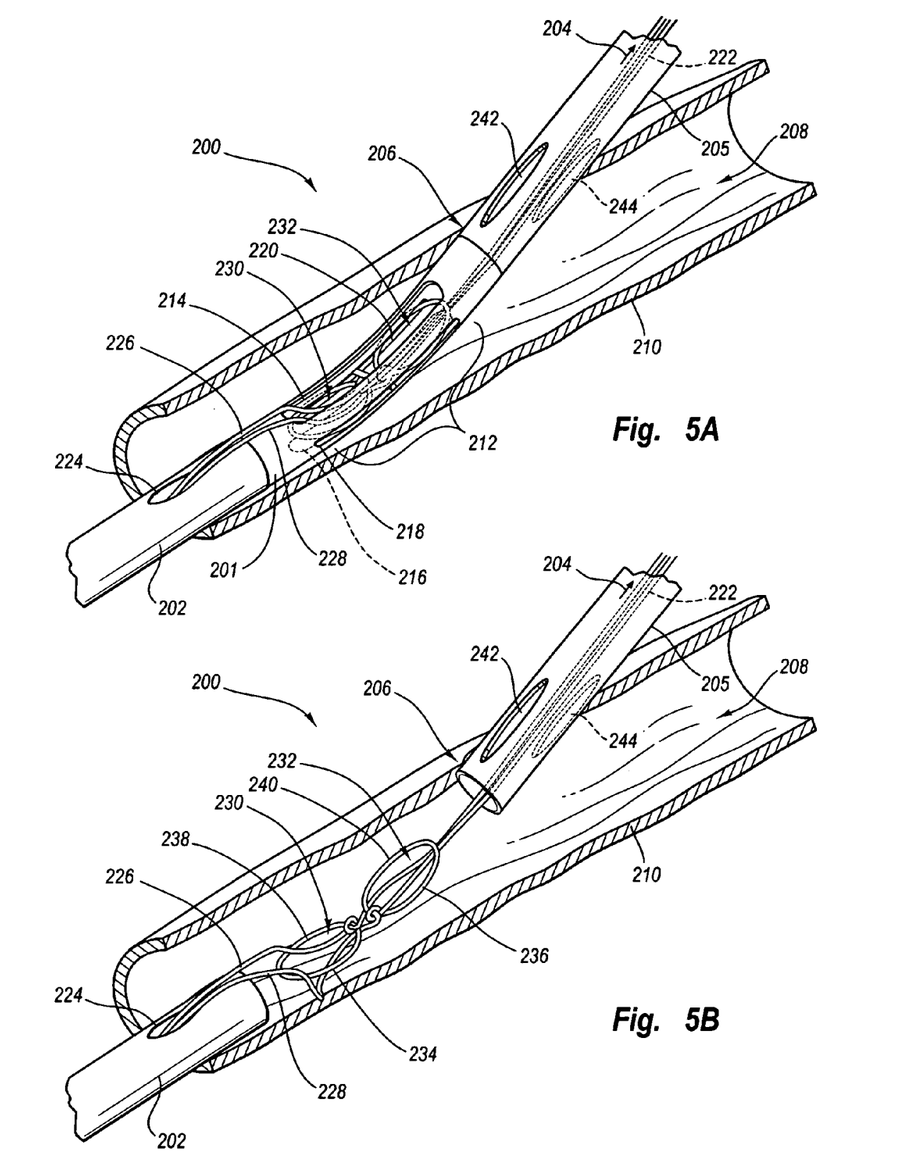
FIG. 5A is a side perspective view, partly in section, of a tissue puncture closure device with a suture loop closure mechanism inserted into an artery according to one embodiment of the present invention.
FIG. 5B is the side perspective view shown in FIG. 5A, with a slotted portion removed to more clearly illustrate the suture knots according to one embodiment of the present invention.

Referring now to FIGS. 5A-5B, a tissue puncture closure device, for example a vascular closure system 200, is shown according to one embodiment of the present invention. The vascular closure system 200 has particular utility when used in connection with intravascular procedures, such as angiographic dye injection, cardiac catheterization, balloon angioplasty and other types of recanalizing of atherosclerotic arteries, etc. as the vascular closure system 200 is designed to cause immediate hemostasis of the blood vessel (e.g., arterial) puncture. However, it will be understood that while the description of the preferred embodiments below are directed to the closure of percutaneous punctures in arteries, such devices have much more wide-spread applications and can be used for closing punctures or incisions in other types of tissue walls as well. Thus, the sealing of a percutaneous puncture in an artery, shown herein, is merely illustrative of one particular use of the vascular closure system 200 of the present invention.

The vascular closure system 200 includes a central shaft or open-loop knot carrying device. According to the embodiment of FIGS. 5A-5B, the open-loop knot carrying device is a carrier tube 201. The carrier tube 201 has a first or distal portion 202 and a second or proximal portion 204. The carrier tube 201 may be made of plastic or other material and is designed for insertion through a vascular access sheath such as insertion sheath 205. The insertion sheath 205 is inserted into a percutaneous puncture such as an arteriotomy 206, and into a bodily lumen 208. According to FIG. 5A, the lumen 208 comprises an interior portion of a femoral artery 210. The carrier tube 201 includes an open slotted portion 212 disposed between the first and second portions 202, 204. According to the embodiment of FIG. 5A, the slotted portion 212 comprises first and second elongated slots 214, 216. The first and second elongated slots are preferable arranged opposite of one another and comprise a width ranging between approximately 5 and 50 degrees of a circumference of the carrier tube

201. As shown in FIG. 5A, the open slotted portion 212 may also include third and fourth elongated slots 218,220 of smaller width than the first and second elongated slots 214, 216. The widths of the third and fourth elongated slots 218, 220 may be approximately equal to one another and range between 1 and 20 degrees of the circumference of the carrier tube 201. The third and fourth elongated slots 218, 220 may be arranged opposite of one another as shown, preferably such that longitudinal centers of the first, second, third, and fourth elongated slots 214, 216, 218, 220 are spaced azimuthally from one another by, for example, approximately 90 degrees.

A filament such as a suture 222 extends from the first portion 202 to the second portion 204, and, as shown in FIGS. 5A-5B, the suture 222 may loop back to the first portion 204. The suture 222 passes through a hole 224 in the first portion 202 and into the slotted portion 212, with one branch 226 entering the slotted portion 212 through the first slot 214 and another branch 228 passing through the second slot 216. The suture 222 is tied into first and second open loop knots 230, 232 that are shown spaced axially from one another and disposed at least partially within the slotted portion 212. FIG. 5B illustrates the first and second open loop knots 230, 232 without the slotted portion 212 for clarity. A first portion 234 of the first open loop knot 230 and a first portion 236 of the second open loop knot 232 extend at least partially though the third slot 218. Similarly, a second portion 238 of the first open loop knot 230 and a second portion 240 of the second open loop knot 232 extend at least partially through the fourth slot 220. Accordingly, the first and second open loop knots 230, 232 are held in an open orientation with respect to the first and second elongated slots 214, 216. The first and second open loop knots 230, 232 are preferably slip knots that are simultaneously closable or tightenable upon placing the suture 222 in tension.

The insertion sheath 205 also includes first and second side ports, for example first and second slots 242, 244, arranged substantially opposite of one another and may be oval-shaped as shown in FIG. 5A. According to the embodiment of FIGS. 5A-5B, the first and second slots 242,244 are adjacent, or within 1-5 cm, of the open slotted portion 212 when the carrier tube 201 is inserted through the insertion sheath 205.

Figure 6:
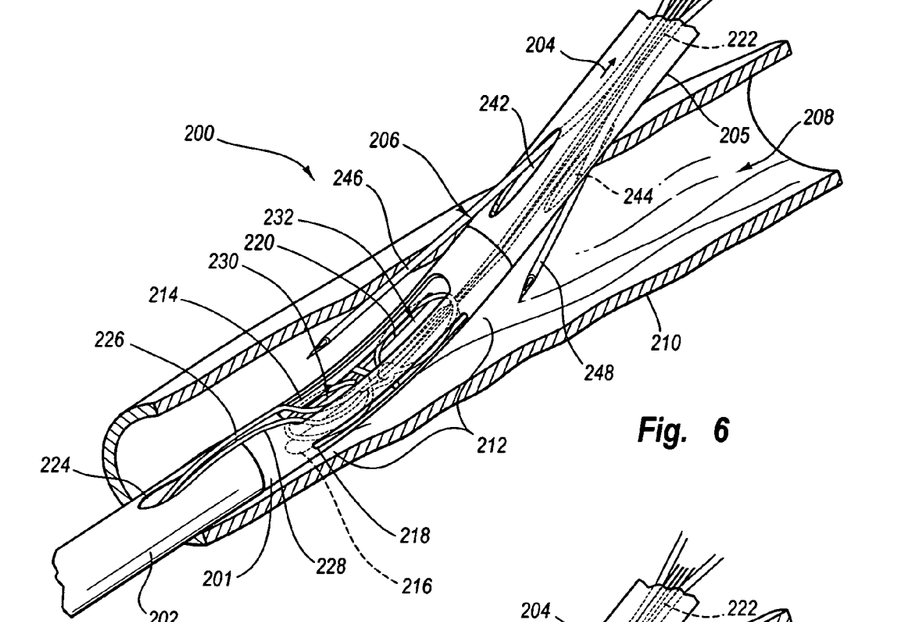
FIG. 6 is a side perspective view, partly in section, of the suture loop closure mechanism shown in FIG. 5A with flanking cannula needles according to one embodiment of the present invention.

Referring next to FIG. 6, the first and second slots 242, 244 in the insertion sheath 205 facilitate passage of first and second cannula needles 246,248, respectively, therethrough. The first and second cannula needles 246, 248 may be have pointed or three-bevel tips as shown. The first and second slots 242,244 in the insertion sheath 205 are aligned rotationally with respect to the first and second elongated slots 214, 216 of the slotted portion 212. The first and second cannula needles 246, 248 diverge from one another and from the insertion sheath 205. The first cannula needle 246 extends further than the second cannula needle 248 such that the first cannula needle 246 provides access to the first open loop knot 230 and the second cannula needle 248 provides access to the second open loop knot 232. As shown in FIG. 6, the first and second cannula needles 246, 248 are insertable through the artery 210 flanking the arteriotomy 206.

Figure 7:
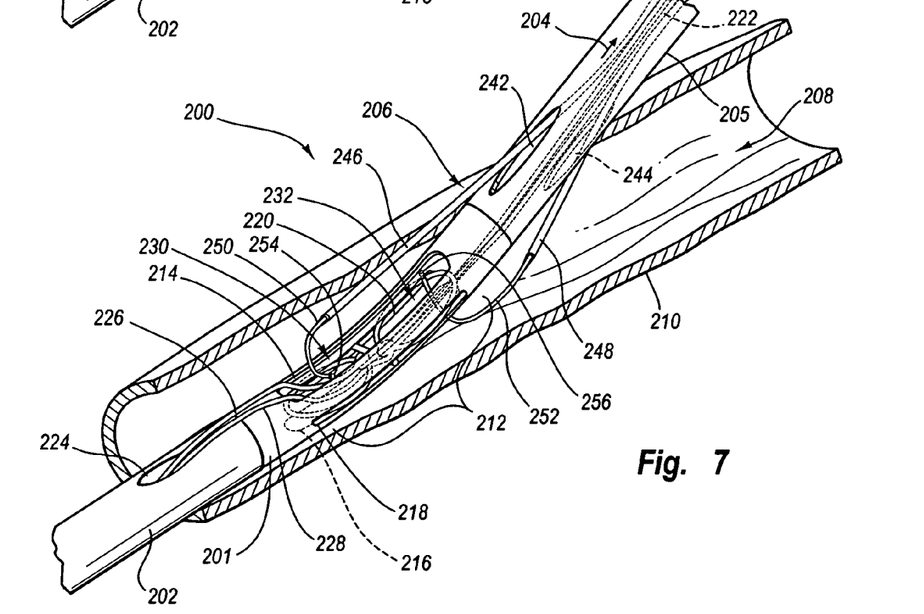
FIG. 7 is a side perspective view, partly in section, of the suture loop closure mechanism shown in FIG. 6 with curved needles extending through the flanking cannula needles according to one embodiment of the present invention.

The first and second cannula needles 246, 248 allow passage of associated first and second curved needles 250, 252 therethrough as shown in FIG. 7. The first and second curved needles 250, 252 are preferably shape-memory needles. Therefore, each of the first and second curved needles 250, 252 is preferably made of a superelastic material such as nitinol and is capable of elastically deforming as it passes through the cannula needles 246, 248. Accordingly, the first and second curved needles 250, 252 may straighten as each passes through its associated cannula needle 246, 248 and gains access to the bodily lumen 208. However, as portions of the first and second curved needles 250, 252 exit the first and second cannula needles 246, 248, they return to the curved configuration shown. A skilled artisan having the benefit of this disclosure will recognize that according to some embodiments, the first and second cannula needles 246, 248 may be omitted, and the first and second curved needles 250, 252 may pass directly through the first and second slots 242, 244 in the insertion sheath 205.

Each of the first and second curved needles 250, 252 includes a step or shoulder 254, 256 at a distal end thereof. The curved shape of the first curved needle 250 facilitates extending the first curved needle 250 into the first elongated slot 214 of the slotted portion 212, and at least partially through the first open loop knot 230. The first curved needle 250 is inserted such that at least the shoulder 254 extends through the first open loop knot 230. Likewise, the curved shape of the second curved needle 252 facilitates extending the second curved needle 252 into the second elongated slot 216 of the slotted portion 212, and at least partially through the second open loop knot 232. As with the first curved needle 250, the second curved needle 252 is inserted such that at least the shoulder 256 extends through the second open loop knot 232.

Figure 8:
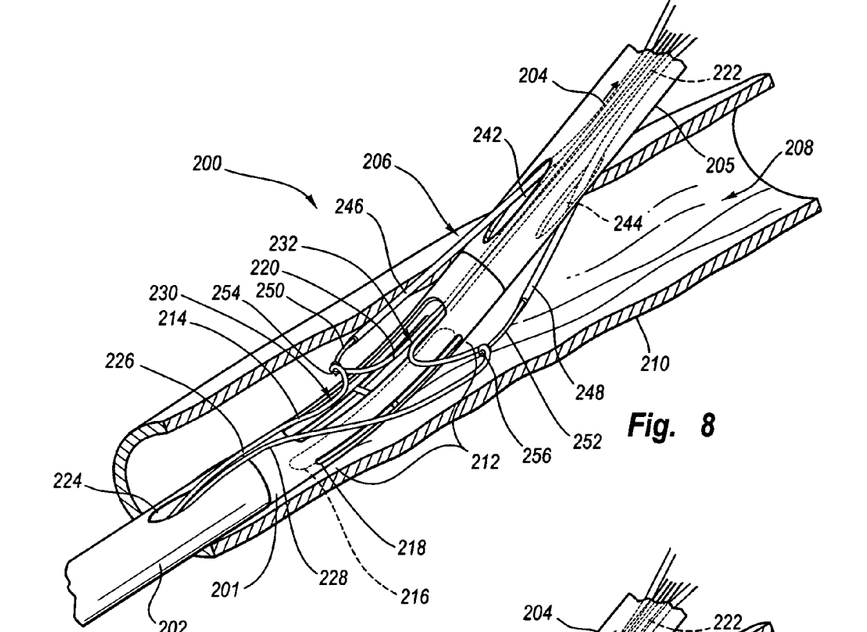
FIG. 8 is a side perspective view, partly in section, of the suture loop closure mechanism shown in FIG. 7 with curved needles extending through the flanking cannula needles and the suture knots tightened around ends of the curved needles according to one embodiment of the present invention.

With the first and second curved needles 250,252 inserted into the first and second open loop knots 230, 232, respectively, the suture 222 may be placed in tension to tighten the knots around the needles as shown in FIG. 8. The first and second knots 230,232 may be remotely tightened by a user pulling on free ends of the suture 222 to place the suture 222 in tension. Thus, the first and second curved needles 250, 252 grab the suture 222. Free ends of the suture 222 may be accessible to an operator by extending the suture 222 from proximal areas of the carrier tube 201 and/or the insertion sheath 205.

Figure 9:
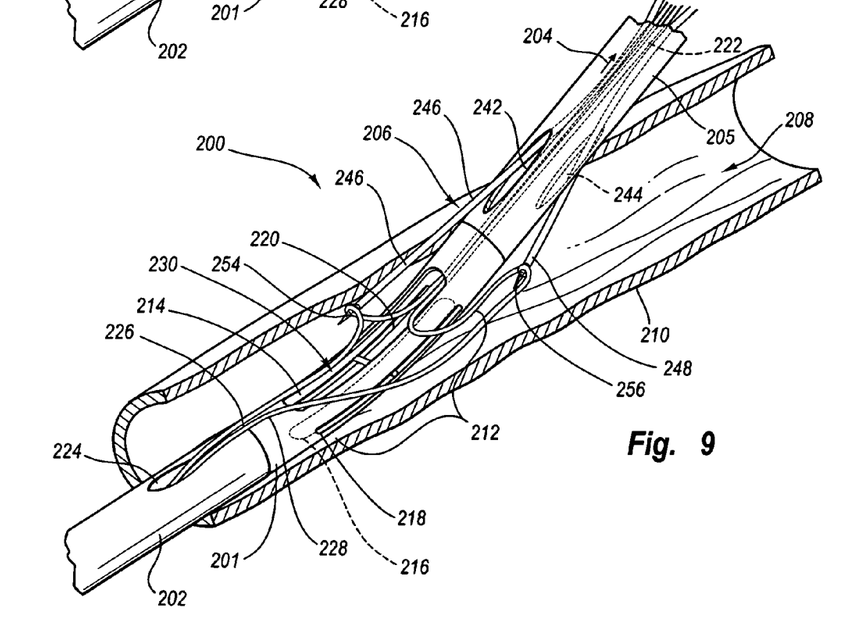
FIG. 9 is a side perspective view, partly in section, of the suture loop closure mechanism shown in FIG. 8 with the curved needles being retracted toward the cannula needles according to one embodiment of the present invention.

Once the first and second knots 230, 232 are tightened around the needles, the first and second curved needles 250, 252 may be retracted at least partially toward the first and second cannula needles 246, 248 as shown in FIG. 9. The first and second knots 230, 232 tend to bear against the shoulders 254,256, which prevent the suture 222 from slipping off of the first and second curved needles 250, 252. The first and second curved needles 250, 252 may be fully retracted through the first and second cannula needles 246, 248, or they may be retracted to the position shown in FIG. 9 such that the first and second knots 230, 232 are arranged just outside of the first and second cannula needles 246, 248.

Figure 10:
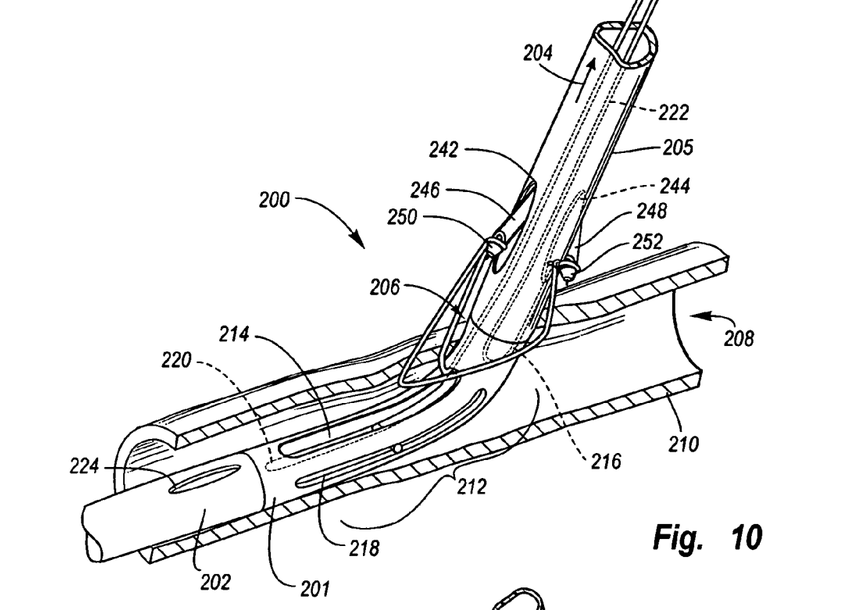
FIG. 10 is a side perspective view, partly in section, of the suture loop closure mechanism shown in FIG. 9 with the cannula needles being retracted according to one embodiment of the present invention.
Figure 11:
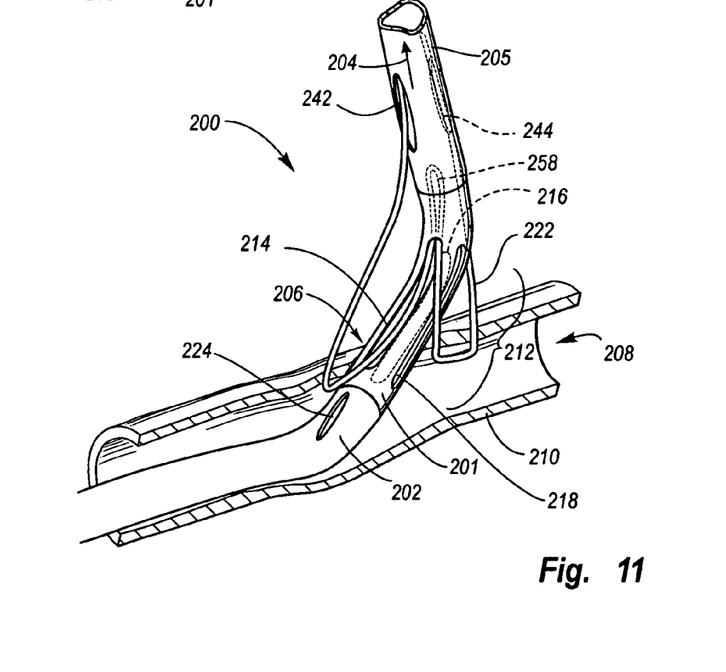
FIG. 11 is a side perspective view, partly in section, of the suture loop closure mechanism shown in FIG. 10 with the suture loop closure mechanism being retracted from the artery according to one embodiment of the present invention.
Figure 12:
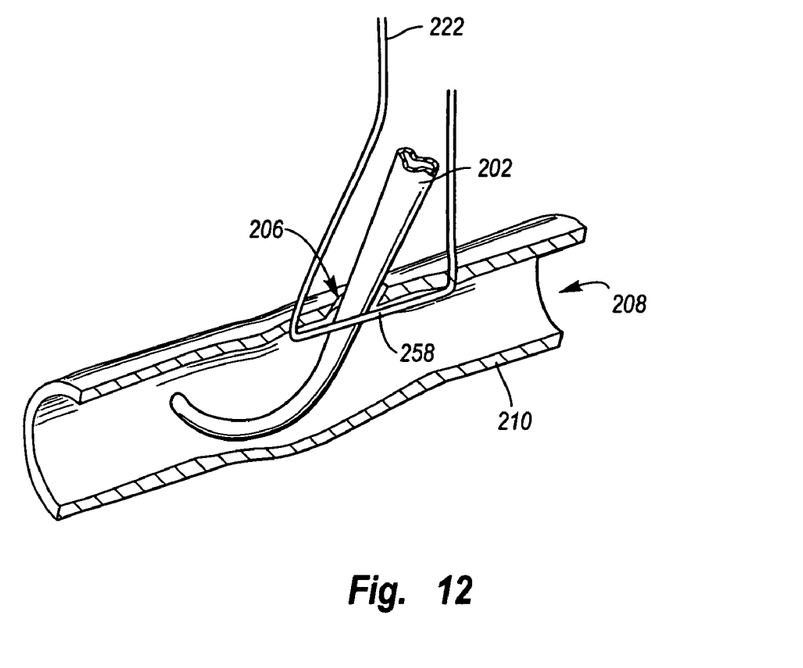
FIG. 12 is a side perspective view, partly in section, of the suture loop closure mechanism shown in FIG. 11 with the suture loop closure mechanism being nearly fully retracted from the artery, leaving the suture extended across the puncture according to one embodiment of the present invention.
Figure 13:
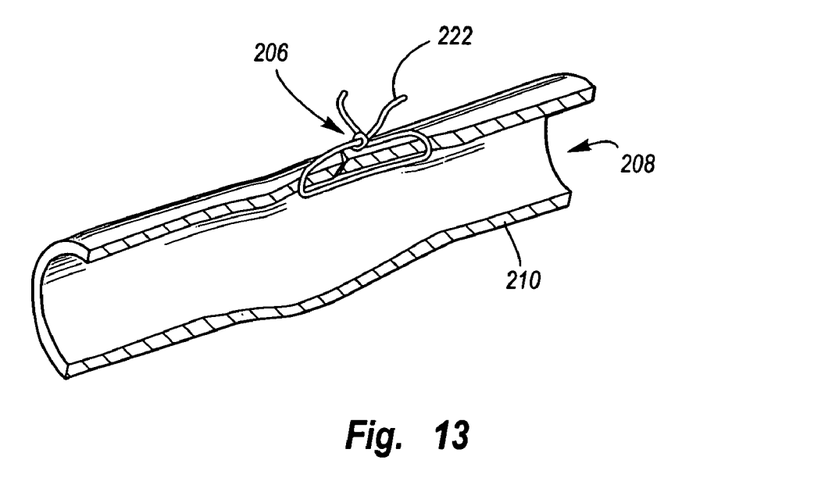
FIG. 13 a side perspective view, partly in section, of the artery with the suture loop closure mechanism of FIG. 12 fully removed from the artery and the suture tied across the puncture according to one embodiment of the present invention.

Following retraction of the first and second curved needles 250, 252, the first and second cannula needles 246, 248 may be simultaneously retracted with the first and second curved needles 250, 252 into the first and second slots 242, 244 in the insertion sheath 205 as shown in FIG. 10. Therefore, the suture 222 is also retracted through the insertion sheath 205 and through the small flanking holes in the artery 210 created by the cannula needles 246, 248 on either side of the arteriotomy 206. The insertion sheath 205 and carrier tube 201 are further retracted from the arteriotomy 206 as shown in FIG. 11, which causes a looped portion 258 of the suture 222 to pass out of the carrier tube 201 and through the slotted portion 212. Eventually, the looped portion 258 extends internally across the arteriotomy 206 as shown in FIG. 12. The vascular closure system 200 is finally removed from the arteriotomy 206 altogether, whereafter the suture 222 may be quickly cut and tied, immediately closing the arteriotomy 206 as shown in FIG. 13.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims. As used throughout the claims and specification, the words "including" and "having," have the same meaning as the word "comprising."

What is claimed is:

1. A tissue puncture closure device, comprising:
    a carrier tube having first and second end portions and a slotted portion disposed between the first and second end portions, the carrier tube defining a lumen;
    a filament extending from the first end portion to the second end portion; the filament including
    lumen of the first and second open loop knots disposed at least partially within the slotted portion;
    wherein the slotted portion extends longitudinally along the lumen, the lumen of the slotted portion comprising first, second, third, and fourth slots arranged around a circumference of the carrier tube with the first and second slots arranged 180 degrees from each other and the third and fourth slots arranged 180 degrees from each other;
    first and second needles arranged to extend from outside the carrier tube through the first and second slots into the first and second open loop knots to grasp the first and second open loop knots.

2. A tissue puncture closure device according to claim 1 wherein the first and second slots are elongated slots.

3. A tissue puncture closure device according to claim 1 wherein the third and fourth slots comprise a smaller width than the first and second slots.

4. A tissue puncture closure device according to claim 1 wherein the third and fourth slots comprise a smaller width than the first and second slots, wherein first portions of the first and second open loop knots extend at least partially through the third slot, and second portions of the first and second open loop knots extend at least partially through the fourth slot.

5. A tissue puncture closure device according to claim 1 wherein the first, second, third, and fourth slots are arranged at approximately 90 degree intervals around the circumference of the carrier tube.

6. A tissue puncture closure device according to claim 1 wherein the central shaft extends through a vascular access sheath, and wherein:
    the first needle includes a first curved needle that extends through a first side port in the vascular access sheath, into the slotted portion, and at least partially through the first open loop knot,
    the second needle includes a second curved needle that extends through a second side port in the vascular access sheath, into the slotted portion, and at least partially through the second open loop knot.

7. A tissue puncture closure device according to claim 1 wherein the central shaft extends through a vascular access sheath, and wherein:
    the first needle includes a first cannula needle that extends through a first side port in the vascular access sheath and diverges from the vascular access sheath, and a first shape-memory needle that passes through the first cannula needle, curves into the slotted portion, and extends at least partially through the first open loop knot;
    the second needle includes a second cannula needle that extends through a second side port in the vascular access sheath and diverges from the vascular access sheath and a second shape-memory needle that extends through the second cannula needle, curves into the slotted portion, and extends at least partially through the second open loop knot.

8. A tissue puncture closure device according to claim 1 wherein the first and second open loop knots are remotely tightenable.

9. A tissue puncture closure device according to claim 1 wherein the first and second open loop knots are spaced from each other axially with respect to the central shaft.

10. A tissue puncture closure device according to claim 1 wherein the filament extends from the second portion back to the first portion in a loop.

11. A tissue puncture closure device, according to claim 1 wherein the first open loop knot is spaced distal of the second open loop knot.

* * * * *